United States Patent [19]

Nicholas

[11] Patent Number: 5,312,984
[45] Date of Patent: * May 17, 1994

[54] AMIDATION OF VINYL CHLORIDE WITH DIMETHYLAMINE USING A SUPPORTED PALLADIUM CATALYST

[75] Inventor: Paul P. Nicholas, Broadview Heights, Ohio

[73] Assignee: The B. F. Goodrich Company, Akron, Ohio

[*] Notice: The portion of the term of this patent subsequent to Oct. 27, 2009 has been disclaimed.

[21] Appl. No.: 950,441

[22] Filed: Sep. 23, 1992

Related U.S. Application Data

[63] Continuation-in-part of Ser. No. 161,710, Feb. 29, 1988, Pat. No. 5,159,113, which is a continuation-in-part of Ser. No. 683,840, Dec. 19, 1984, abandoned.

[51] Int. Cl.$^5$ .............................................. C07C 231/10
[52] U.S. Cl. ...................................... 564/132; 564/205
[58] Field of Search ................................. 564/132, 205

[56] References Cited

U.S. PATENT DOCUMENTS

| | | | |
|---|---|---|---|
| 3,988,358 | 10/1976 | Heck | 546/316 |
| 4,128,554 | 12/1978 | Heck | 546/317 |
| 5,159,113 | 10/1992 | Nicholas | 564/132 |

FOREIGN PATENT DOCUMENTS

| | | | |
|---|---|---|---|
| 57-122055 | 7/1982 | Japan | 564/132 |
| 58-213724A | 12/1983 | Japan | 564/132 |

OTHER PUBLICATIONS

Komoroski et al, Inorganic Chemistry, 1986, 25, 3917–3925.

Primary Examiner—Glennon H. Hollrah
Assistant Examiner—Shailendra Kumar
Attorney, Agent, or Firm—Alfred D. Lobo; Nestor W. Shust

[57] ABSTRACT

A continuous process for making N,N-dimethylacrylamide (NNDMA) is disclosed which uses a commodity chemical, namely vinyl chloride (VCl), which is amidated with dimethylamine (DMA) and carbon monoxide in the presence of a supported palladium(O) triorganophosphine catalyst used under conditions where the ratio of P/Pd is critical. The continous process unexpectedly provides the catalyst with long life because the reaction can be carried out in a moving bed of catalyst in the presence of enough acetonitrile solvent to prevent deposition of DMA.HCl, formed during the reaction, in the pores of the catalyst support.

16 Claims, 1 Drawing Sheet

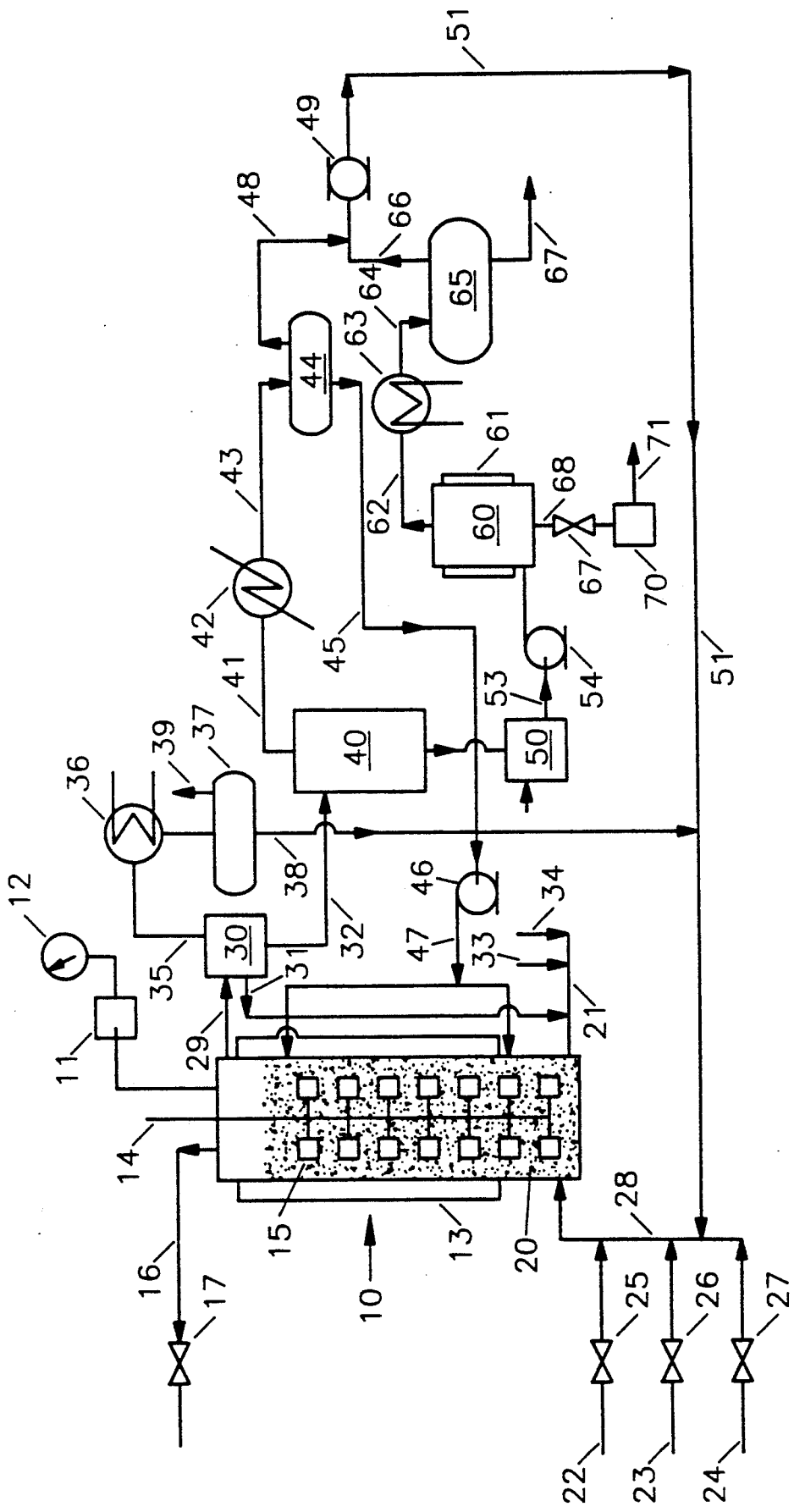

AMIDATION OF VINYL CHLORIDE WITH DIMETHYLAMINE USING A SUPPORTED PALLADIUM CATALYST

BACKGROUND OF THE INVENTION

Cross Reference to Related Application

This application is a continuation-in-part application of Ser. No. 161,710 filed Feb. 29, 1988 now U.S. Pat. No. 5,159,113 which, in turn, is a continuation-in-part application of Ser. No. 683,840 filed Dec. 19, 1984, now abandoned.

This invention relates to a process for the amidation of vinyl chloride (VCl) with dimethylamine $HN(CH_3)_2$ (DMA) to yield N,N-dimethylacrylamide (NNDMA) essentially quantitatively. Among numerous amines, dimethylamine undergoes a surprisingly effective reaction when a palladium(O) triorganophosphine catalyst is used under specified conditions which unexpectedly also provide the catalyst with long life. An analogous reaction would occur with other lower $C_2-C_5$-dialkylamines. Amidation refers to the known reaction of an amine with carbon monoxide (CO), under elevated temperature and pressure, to produce an amide. The parent case provided data which proved that there was more than an order of magnitude difference in the rate of amidation of VCl compared with that of structurally similar vinylic chlorides.

Dimethylamine is capable of reducing $Pd^{2+}$ to $Pd^0$ rapidly under amidation conditions, such that $PdCl_2(PPh_3)_2 + 2(PPh_3)_2$ is equivalent to $Pd(PPh_3)_4$, and this ability enables VCl to be amidated with DMA using the $Pd^{+2}$ catalyst. Additional details of the amidation of VCl with an amine, relevant comparisons of reactions with other chloroalkenes, and the manner of identification of intermediates and products of the reaction, are set forth in my article titled "Amidation of Chloroalkenes Catalyzed by Tertiary Phosphine Complexes of Palladium(O)" in *J. Org. Chem.* 1987, 52, 5266–5272, the disclosure of which is incorporated by reference thereto as if fully set forth herein.

It was not known that a solid, particulate catalyst support containing chemically bound phosphines for coordination to palladium, provides a basis for a continuous amidation process, preferably in a stirred bed, in which process the catalyst can be readily separated from the reaction products. The retention of palladium is high, even over long reaction times, and it is expected to be less susceptible to degradation than the unsupported catalyst. Recovery and reuse of the catalyst (referred to as a heterogeneous catalyst) together with low toxicity are additional benefits.

As will be obvious to one skilled in the art, the introduction of even an inert support in the adaptation of a reaction known to occur under homogeneous conditions, introduces a wide range of new variables. Therefore, the basic disclosures relating to investigations of effective catalysts are generally from studies performed under homogeneous conditions; and this was done by me in the parent case as it was by Richard F. Heck in U.S. Pat. Nos. 3,988,358 and 4,128,554 issued to him.

A fortuitous investigation of phosphinated supports by the inventor and coworkers led to the idea that it might be worth trying to adapt such a support for use with the Pd(0) catalyst which had been found to be so effective in this amidation reaction of VCl with dimethylamine. This investigation was published in an article entitled "$^{31}P$ and $^{13}C$ Solid-State NMR of Tertiary Phosphine-Palladium Complexes Bound to Silica" by Richard Komoroski, Angelo Magistro and Paul Nicholas in *Inorg. Chem.* 1986, 25, 3917, the disclosure of which is incorporated by reference thereto as if fully set forth herein. This article detailed the characteristics of phosphine-to-palladium bonds within such supports. However, there was no information to help predict if Pd would be retained under different reaction environments, nor how effectively a heterogeneous catalyst derived from a phosphinated support might perform under the conditions of an amidation reaction, such as the one described herein.

The lack of an economically attractive catalyst support is one of the reasons why the commercial promise of amidation reactions obtained with known catalysts has never materialized. Among other obvious reasons is the discouragingly low reaction rates with all but the organobromides and organoiodides which are of little commercial significance. Thus, over the years, those skilled in the art had a well-established experimental basis for eschewing further investigation of amidation applied to chloroalkenes and chloroarenes, irrespective of the catalyst system used.

Particularly with respect to synthetic resinous catalyst supports, the proper choice is one which not only affords an active Pd catalyst, but which also has a large pore diameter which becomes still larger when swollen with VCl. By chance, the catalyst derived from such a support provides a profusion of active sites and facilitates transport of reactants and products. The phosphination of crosslinked polystyrene is known. But to be preparatively useful, sufficient swelling must be provided by VCl to achieve high rates of conversion, avoid plugging the pores of the support, and avoid severe weakening of the catalyst under process conditions. The successful amidation of VCl with DMA also requires recovery of the catalyst.

Turning to inorganic polymers such as silica or silica-alumina mixtures, it is apparent that they do not swell in VCl. If one were instructed to do so, one could prepare a support having a specific pore volume and defined surface area. However phosphination of such a support must be achieved through OH groups, and the OH content in such supports is typically low.

Considering the numerous options available for functionalizing the inorganic oxide to be readied for use as an effective support, even supplied with the foregoing information on phosphination, one would have no basis to choose which would be effective. Nor would one have a basis to determine if the relatively few phosphine ligands attached through these OH groups would have sufficient capacity to sustain a fast and selective amidation reaction, irrespective of the mechanism of the reaction.

In a supported catalyst containing bound phosphine ligands, it will be recognized that the immobilization of Pd by the ligands is essential for catalyst longevity. But there is no basis to expect that such immobilization will be adequate, or that if it was, that the activity of the homogeneous analog of the catalyst will be replicated. For example, only the monomeric form of titanocene hydrogenation catalyst is active. In solution, however, the catalyst is in equilibrium with its dimer and other aggregates, all of which are inactive.

In view of the foregoing considerations it was concluded that there are many factors which can, and do, alter the reactivity of a catalyst when its ligands are bound to the polymer, whether the polymer is organic or inorganic. Such factors include restricted motion; nonuniform local environments; a distribution of coordination geometries due to ligands being located at sites which cannot comply with ideal coordination geometries; and restricted solvation. The recognition that coordination geometries of palladium chloride complexes of silica-bound phosphines are, coincidentally, similar to simple phosphine complexes, provided much of the incentive to investigate the effectiveness of the phosphine complexes of Pd(0) on a silica-supported catalyst in the amidation of VCl with dimethylamine (DMA).

Additional incentive is derived from the fact that NNDMA is prepared by the reaction of ethyl acrylate with DMA and produces the same intermediate as the Michael adduct from the amidation of VCl with dimethylamine:

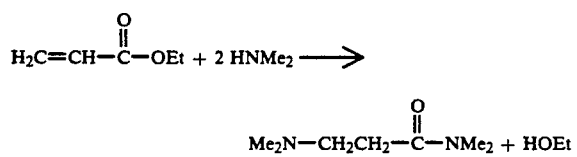

The adduct is then thermally cracked to produce N,N-dimethylacrylamide, CH2=CHCONMe2, represented by the reaction

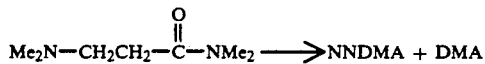

where Et and Me represent ethyl and methyl respectively.

NNDMA is a mobile, water white liquid having a boiling point (bp) of 81° C. at 21 mm Hg and a freezing point of -40° C. It is stable and completely miscible with water and most organic solvents including acetone, benzene, chloroform, ethylacetate, ethyl alcohol, ethylene dichloride, methyl alcohol, tetrahydrofuran (THF), toluene and xylene. NNDMA is in particular demand because it is easily polymerized by free radical and anionic initiators, the structure of the polymers being dependent upon the catalyst chosen. Free radical initiators are most preferred and they produce clear, tough thermoplastic polymers which are soluble not only in water but also in many solvents. NNDMA is an attractive monomer because its copolymers have desirable dyeability, anti-static properties, water permeability and adhesion. Copolymers can be prepared with numerous vinyl monomers, including styrene, acrylonitrile, acrylamide and substituted acrylamides, acrylic acid, methacrylic acid and their esters, inter alia. A lower cost NNDMA would be commercially important and would encourage broader investigation of its many polymers. A process for making NNDMA based on VCl offers that potential.

The amidation of VCl with DMA produces solid dimethylamine hydrochloride (DMA.HCl) which can deposit in the pores of the catalyst and quickly shut down the amidation reaction. The continuous production of NNDMA by the amidation of VCl with DMA was critically dependent upon finding a solution to this problem, without otherwise adversely affecting the speed of the reaction or the recovery of the Michael adduct from which the NNDMA was eventually to be obtained.

The particular promise of VCl amidation with DMA is based on the unexpectedly high rate of the rate-controlling oxidative addition step. The NNDMA produced is rapidly and quantitatively converted to the Michael adduct 3-dimethylamino-N,N-dimethylpropanamide, with DMA. Adduct formation occurs only with VCl and no other chloroalkene, with unexpectedly high selectivity, while maintaining excellent catalyst performance. Combined with the extended catalyst life when VCl amidation is performed with DMA and ease of recovery of the supported catalyst, this process affords a practical route to the manufacture of dimethylacrylamide. The unique reaction with a heterogeneous catalyst, and the greatly enhanced catalyst stability, is due to the discovery that dimethylamine is able to overcome the causes of deactivation which I have identified.

More specifically, this invention relates to the use of known Pd(II) complexes of polymer-bound tertiary phosphines in the amidation of VCl with DMA, which reaction forms the Michael adduct. The adduct, derived from the addition of DMA to NNDMA, is then conveniently and efficiently converted to the desired NNDMA.

This amidation process involves a series of reactions in which the key step is the oxidative addition of Pd(0) to the organohalide. It is well-known that oxidative addition occurs far more rapidly with bromides and iodides than with chlorides. In the art, the only example of a monochloroalkene undergoing amidation to an alpha-beta unsaturated amide is that of 2-chloropropene disclosed in U.S. Pat. Nos. 3,988,358 and 4,128,554 to Heck.

Heck's investigation of the amidation reaction was generally limited to atmospheric pressure and a temperature in the range from 60°-100° C. (see first line of "Results and Discussion" of the article entitled "Palladium-Catalyzed Amidation of Aryl, Heterocyclic, and Vinylic Halides" by A. Schoenberg and R. F. Heck, J. Org. Chem. 1974, 39 3327 and examples in the '358 and '554 patents).

With reference to rates, the Heck disclosure relates to any vinyl or aryl halide, specifically covering chlorides, bromides and iodides, without suggesting that there may be any distinguishing characteristics in the reactivity of one halide over the other that would be critically important to their commercial significance.

Among the numerous organic halides and amines disclosed, there was no indication that the amidation of VCl with dimethylamine might be unique. Further, there was no indication that any suggested reaction might benefit from being supported on a porous catalyst surface, nor why it should be. Thus, there was no suggestion that any of the amidations disclosed, and specifically, the amidation of VCl with dimethylamine on a catalyst having covalently bonded phosphine ligands, might be particularly effective.

That there should be a notable difference in the rates of amidation among various non-allylic halides is expected. This is especially true when comparing bromides and iodides with chlorides and fluorides. The difference in rates between chlorides on the one hand, and bromides and iodides on the other, is confirmed by comparing rough estimates of rates calculated from Heck's examples. These are estimates because the Heck experiments with 2-chloropropene were directed to determining yields, the stated objective to the contrary. His experiments were carried out to unspecified high conversions of aniline, the limiting reagent. Therefore, when comparing rates of product formation among the bromides, iodides, and 2-chloropropene, one must assume that the reported reaction times correspond to the time required to reach roughly the same aniline conversion. Such a comparison shows a substantially slower rate for 2-chloropropene despite more vigorous conditions.

In my experiments I have measured the continuous disappearance of dimethylamine with time and expressed this as "turnover rate". The turnover rate used herein is defined as:

(moles of dimethylamine converted) divided by (moles of active catalyst) for each hour of reaction time.

This form of measuring rate as "turnover rate" was used in the parent application, and is routinely used in the art (see, for example, "*Catalysis and Inhibition of Chemical Reactions*", by P. G. Ashmore, Butterworths, London, 1963, pp 9).

In the illustrative examples that I have presented for VCl amidation, I have reported the rate of disappearance of DMA simply because this rate can be measured continuously by gas chromatography.

Though not relevant to the invention claimed herein, the rates reported in the Heck references for different amidation reactions may be compared with those I obtained if they are converted to "turnover rate" with the appropriate assumptions. Heck's reports focused more on yield than on catalyst longevity or rates. However, yield data alone, are not sufficient to assess the practical merits of the process.

When comparing the amidation rate of each of three chloropropenes with VCl using ammonia, it was shown in the parent application that amidation of VCl was orders of magnitude faster than that of the chloropropenes. An explanation of the low rates obtained with 2-chlorpropene is that the oxidative addition step, which activates the carbon-halogen bond in this process, is very slow for vinyl or aromatic carbon-X bonds when X is Cl, compared with Br or I. For this reason, bromides and iodides are usually used when this activation step is required in a chemical reaction. Thus, lactams are prepared from bromoalkenes and iodoalkenes having secondary substituents. See M. Mori, et al *J. Org. Chem.* 1983, 48, 4058. Benzolactams are prepared from o-bromoaminoalkylbenzene by photochemical carbonylation under phase transfer conditions using cobalt carbonyl as the catalyst. See J. Brunet, et al. *J. Org. Chem.* 1983, 48, 1166. All but one of the many examples in the Heck references relate to bromides and iodides. The resistance of chloroalkyls, monochloroalkenes and chloroarenes toward oxidative addition with zero-valent Ni, Pd and Pt complexes is well documented. See P. Fitton, et al *J. Organomet. Chem.* 1971, 28, 287; J. T. Colman, et al *Principles and Applications of Organotransition Metal Chemistry* 1980, 185; and, R. F. Heck, et al *Catalysis in Organic Synthesis* 7th ed. 1978 1980 195–218, inter alia.

The presence of the methyl group in 2-chloropropene is the reason for the low reaction rate. It also suppresses formation of the Michael adduct derived from addition of the amine to the acrylamide produced. VCl is unique among monochloroalkenes, being the only unsubstituted member. Heck did not discover that VCl would give the high reaction rate and form the Michael adduct. Though he includes VBr in his broad disclosure of useful reactants, there is nothing in his disclosure to suggest that VBr may behave differently from the host of other compounds since there is no mention anywhere, of the Michael adduct. Not having run VBr or VCl, he could not know that the formation of the Michael adduct depends upon the unique unsubstituted character of VCl or VBr, and that it has an important influence on catalyst stability. The Michael adduct is critical to catalyst stability because it suppresses formation of the phosphonium chloride which removes stabilizing ligand from the metal in the complex, thus causing the metal to separate.

Moreover, Heck added a stoichiometric amount of tri-n-butylamine to remove HCl from the intermediate when amidation was performed with a weakly basic amine such as aniline. This was claimed to be a necessary condition to carry out the Heck invention in such instances. It is, however, unnecessary in VCl.

Still another difference that I have observed relates to the role of the amine as the reducing agent for the catalyst complex. In every Heck example, the catalyst used was a $Pd^{2+}$ complex (e.g. $Pd(PPh_3)_2Cl_2$) which was undoubtedly reduced to the active $Pd(0)$ complex in situ. I have found that the amine is the principal reducing agent for this process, at least with VCl, and that a suitable amine is one that contains alkyl substituents having α-hydrogen atoms. Thus, while either $Pd(PPh_3)_2Cl_2 + 2PPh_3$ or $Pd(PPh)_4$ are equivalent catalysts when dimethylamine is the amine reactant, they are not equivalent when using ammonia. $Pd(PPh_3)_2Cl_2$ is essentially inactive in VCl amidation with ammonia as shown in example 7 in the parent case. Therefore, Heck's disclosure with the catalyst he used, is not an enabling disclosure in this case. The choice of amine is also an important factor in catalyst activity and longevity, depending upon the extent to which $Pd(PR_3)_2Cl_2$, defined herebelow, forms during amidation as described below. In this respect also, DMA is the amine of choice.

Had Heck run the reaction with VCl instead of 2-chloropropene, he would have observed its high reactivity, the formation of the Michael adduct, its importance to catalyst stability, and reported the results.

SUMMARY OF THE INVENTION

It has been discovered that a critical ratio of P/Pd in the range from 1.5 to 4 is highly effective in a heterogeneous, porous catalyst, containing covalently bonded tertiary phosphines which form coordination complexes with Pd(II) or Pd(0). The highly effective amidation reaction capitalizes on the unique requirements for the amidation of VCl with CO and DMA. A particularly effective bound phosphine is triphenylphosphine.

The reaction product with VCl is mainly the Michael adduct of DMA with the NNDMA (N,N-dimethylacrylamide) produced. The formation of this adduct has an important influence on the stability of the catalyst because it competes with and suppresses the corresponding addition of the tertiary-phosphonium ligand from the catalyst complex. The latter reaction produces small amounts of a (2-carbamoylethyl)triphenylphosphonium chloride, and the resulting loss of ligand causes palladium metal to separate, thereby deactivating the catalyst. In addition, the reaction produces DMA.HCl (dimethylamine hydrochloride) which can precipitate within the catalyst, plug the pores, and shut down the reaction.

It is, therefore, a general object of this invention to provide a continuous two step process in which the Michael adduct is first formed in the porous catalyst without plugging the pores with DMA.HCl formed. In the second step, the Michael adduct is thermally reversed to NNDMA and DMA.

It is a specific object of this invention to provide a process for the amidation of VCl in a two-step process comprising, in a first step, reacting VCl and CO with dimethylamine in the presence of a catalytically effective amount of a Pd(0) triorganophosphine complex covalently bound to the porous support, either charged as such or produced in situ from a Pd(II) complex under the reaction conditions, to form a Michael adduct of DMA and NNDMA in the presence of sufficient solvent to maintain DMA.HCl in solution; and, in the second step, heating the Michael adduct to recover the dimethylacrylamide.

It has also been discovered that, as in the parent case which teaches the use of a homogeneous catalyst, amidation of VCl with CO and DMA is fast and maintains high conversions. The continuous process particularly benefits from the continuous removal of reaction products as they are formed, so as to prevent their accumulation sufficient to foul the catalyst. Further, unreacted VCl and DMA recovered from thermally cracking the Michael adduct, are recycled so that the cost of reactants is kept to a minimum.

It has further been discovered that in the phosphinated catalyst found to be effective in the amidation of VCl with DMA, the ratio of P/Pd in the range from 1.5 to 4, preferably 2 to 4, is uniquely effective to provide essentially quantitative yields and excellent rates of reaction.

It is therefore a specific object of this invention to provide a process in which the ratio of P/Pd in the supported catalyst is controlled in the range from 2 to 4.

It is another specific object of this invention to provide a continuous Pd(0)-catalyzed process for VCl amidation with DMA and CO, which process yields NNDMA essentially quantitatively.

It is still another specific object of this invention to provide a continuous process for the catalytic production of NNDMA, comprising, reacting a stoichiometric excess of VCl and CO with DMA in the presence of a catalytically effective amount of a heterogeneous catalyst consisting essentially of a porous support having covalently bonded triorganophosphines forming coordination complexes with Pd(0) or a Pd(II) complex capable of being reduced to Pd(0) under amidation conditions, the Pd(0) complex having the stoichiometry:

$Pd(PR_3)_n$ 

wherein R represents $C_1$-$C_4$ lower alkyl, phenyl, $C_1$-$C_4$ alkylphenyl, and cycloalkyl having 4 to 6 ring carbon atoms;

n is an integer in the range from 2 to 6, and, when n>4, excess ligand is present;

in a reaction zone at a temperature in the range from above 80° C., to a temperature below which the Michael adduct dissociates, and under a pressure in the range from about 200 psig but below 600 psig, to form a major amount, on a molar basis, of the Michael adduct of the DMA with the NNDMA in the presence of a solvent for DMA.HCl;

recovering the Michael adduct and DMA.HCl together from the reaction products of reaction, and venting excess CO;

separating the solvent from the Michael adduct and DMA.HCl and returning the solvent to the reaction zone;

adding a sufficient amount of an inorganic aqueous alkali to neutralize the DMA.HCl and form an inorganic salt;

recovering the inorganic salt;

heating the Michael adduct to above its dissociation temperature to form NNDMA and DMA; and, cooling the NNDMA and DMA at a temperature above that which will provide favorable conditions for the Michael adduct to be re-formed;

recovering the NNDMA; and, returning the DMA produced from the Michael adduct to the reaction zone.

BRIEF DESCRIPTION OF THE DRAWING

FIG. 1 is a flowsheet schematically representing the main steps in the amidation of VCl with DMA and CO, and the recovery of unreacted reactants and catalyst, both of which are recycled to provide the basis for an economically attractive process.

DETAILED DESCRIPTION OF PREFERRED EMBODIMENTS

The reaction proceeds at a temperature from above about 80° C. to a temperature below that required to dissociate the Michael adduct to the corresponding acrylamide. The preferred temperature range is from 80° C.-150° C., it being advantageous to carry out the reaction at high temperature without deleteriously affecting the catalyst. Most preferred is a range from 100° C. to 120° C. The pressure is superatmospheric being in the range from above about 200 psig but below 600 psig, depending upon the temperature at which the reaction is performed. Formation of the adduct from the amine and the amide formed during the reaction is a specific condition which enhances catalyst longevity by suppressing the addition of phosphine ligand with which it competes. Thus, the combination of a large amount of a highly nucleophilic amine together with low concentrations of a moderately nucleophilic, polymer-bound triorganophosphine ligand leads to high catalyst stability. A particularly effective ligand is triphenylphosphine.

The catalyst support may be microporous or macroporous, organic or inorganic, having an average pore size in the range from about 50 Å to about 2000 Å, depending upon whether the support is organic or not. A typical microporous inorganic support is tailored to have an average pore size in the range from about 50 Å to about 100 Å, preferably in the size range form 80 Å to 100 Å; an organic support is typically macroporous and has an average pore size in the range from about 500 Å to about 2000 Å prior to being swollen. The surface area of the support may be in the range from 10 to about 500 m²/gm, an inorganic support characteristically having a surface area which is in the upper portion of the range, and an organic support an area in the lower portion. Organic supports preferably have a surface area in the range from 20 to about 100 m²/gm.

Inorganic supports are preferably siliceous, particularly silica or silica alumina; organic supports are preferably a crosslinked vinylaromatic homopolymer or copolymer which is swellable but substantially insoluble in vinyl chloride at the temperature range in which the reaction is to be performed. Most preferred is polystyrene crosslinked with 3 mol % vinylbenzene, which crosslinked polymer has an average pore size in the range from 700–900 Å, a surface area of about 50 m$^2$/gm and a particle size in the range from about 300–800 μm.

In the most preferred embodiment, NNDMA is manufactured by the amidation of vinyl chloride in a reaction utilizing a heterogeneous catalyst consisting essentially of monodentate triorganophosphine ligands covalently bound to the support which forms complexes of palladium(O) having the stoichiometry:

$$Pd(PR_3)_n$$

wherein,

R represents $C_1$–$C_4$ lower alkyl, phenyl, $C_1$–$C_4$ alkylphenyl, and cycloalkyl having 4 to 6 ring carbon atoms; and, n is an integer in the range from 1.5 to 6, preferably from 2 to 6; and, when n>4, excess ligand is present.

An authentic Pd(0) complex may be used. Such a catalyst could be made by contacting the phosphinated support with the Pd(0) complex, $Pd_3(TBAA)_3CHCl_3$ (where TBAA is an acronym for tribenzylidene acetylacetone) as generally described by Ishi, Y., et al, in *J. Organomet. Chem.* 1974, 73, 411, with the required amount of phosphine ligand to obtain the desired stoichiometry. Alternatively, a Pd(II) complex may be used, e.g., $Pd(PR_3)_2X_2$, where X=halogen, if the amine used in the amidation reaction contains an α-hydrogen. The amine, thereby, also serves as a reducing agent to produce the active Pd(0) complex under amidation conditions. The latter is preferred due to the ease of handling Pd(II) complexes compared with Pd(0).

The desired overall amidation reaction is represented as follows:

$$CH_2=CHCl + CO + 2HNMe_2 \xrightarrow{(cat)}$$
$$CH_2=CHCONMe_2 + Cl^-H_2N^+Me_2$$

wherein Me represents $CH_3$ (methyl).

The ideal reaction proceeds stepwise on the heterogeneous catalyst, as is represented below for DMA:

$$H_2C=CHCl + CO + 2HNMe_2 \xrightarrow{PdL_n}$$
$$L=ligand$$
$$H_2C=CHCONMe_2 + H_2NMeCl$$
$$H_2C=CHCONMe_2 + HNMe_2 \longrightarrow$$
$$Me_2NCH2CH2CONMe_2$$
$$H2C=CHCl + 3HNMe_2 + CO \longrightarrow$$
$$Me_2NCH2CH2CONMe_2 + H_2NMe_2Cl$$

The reaction products are identified as the Michael adduct, 3-dimethylamino-N,N-dimethylpropanamide, N,N-dimethylacrylamide, and dimethylammonium chloride.

The Michael adduct is preferably heated (cracked) under reduced pressure to a temperature in the range from about 160° C. to about 200° C. to yield dimethylacrylamide, $$Me_2NCH2CH2CONMe_2 \rightarrow Me_2NH + H_2C=CH-CONMe_2$$

A comparison of VCl amidation with DMA and with ammonia under homogeneous conditions, is indicative of the unique activity of DMA. During amidation with ammonia, the deactivation of $Pd(PPh_3)_4$ usually occurs within a few hundred turnovers (number of moles of VCl converted, divided by number of moles of catalyst). This is accompanied by the formation of the phosphonium salt and colloidal metallic Pd. The consumption of tertiary phosphine in this way causes Pd to cluster and precipitate. Though catalyst life can be extended with increasing PPh$_3$/Pd ratios, deactivation eventually occurs. Accordingly, complexes of more nucleophilic tertiary phosphines deactivate faster and form phosphonium salt more rapidly. When catalyst activity is prolonged with increased PPh$_3$/Pd ratios, small amounts of $Pd(PPh_3)_2Cl_2$ and 1,3-butadiene are also detected among the products. Therefore, this slow reaction is also able to make a measurable contribution toward deactivation during amidation with ammonia.

Dimethylamine affords far greater catalyst stability than ammonia, stemming from its ability to overcome the two identified causes of deactivation. First, the Michael addition of dimethylamine to N,N-dimethylacrylamide occurs much faster than phosphonium salt formation. Secondly, unlike ammonia, dimethylamine is able to rapidly reduce $Pd(PPh_3)_2Cl_2$ to the active catalyst, such that $Pd(PPh_3)_2Cl_2 + 2PPh_3$ is catalytically equivalent to $Pd(PPh_3)_4$. Thus to the extent that some coupling occurs and produces $Pd(PPh_3)_2Cl_2$, it is not as damaging a side reaction with dimethylamine as it is with ammonia. For these reasons, more than 1000 turnovers (moles of dimethylamine per mole of catalyst) have been achieved with dimethylamine without catalyst deactivation.

This invention is unexpectedly effective when practiced in a continuous process schematically illustrated in the flowsheet shown in FIG. 1, wherein a glass-lined tubular reactor, identified generally by reference numeral 10, is provided with a rupture disc 11 and pressure gauge 12. The reactor is jacketed with an electric heater 13 which provides adequate control of the temperature within the reactor. A paddle stirrer 14 with radial arms carrying arcuate paddles 15 is centrally axially disposed within the reactor to provide a gentle stirring action which gradually raises supported catalyst 20 and reactants to the top of the reactor. Another suitable reactor is one with helical ribbon agitators of double flight design. The sloped surfaces of the ribbons moving near the vessel wall produce not only a tangential movement of fluid, but also axial and radial flow. Stagnant regions are eliminated and optimum heat transfer is obtained. A vacuum line 16 provided with a valve 17 allows the reactor to be evacuated prior to purging with nitrogen and loading the catalyst. The supported catalyst is loaded into the reactor in the form of a granular or powdery mass in the size range smaller than about 850 μm, carried in nitrogen gas through charging conduit 21 to form, and be operated as a moving bed. The preferred size range is from 10–150 μm (0.01–0.15 mm) for inorganic supports and 200–850 μm for organic supports, The reactor is pressurized with CO and filled with liquid VCl under pressure and the desired amount of acetonitrile to maintain a preferred ratio of VCl to acetonitrile during operation. VCl is both a reactant and a solvent which provides the reaction medium. Conduit 21 is used to add make-up catalyst, as required, during operation of the reactor. Nitrogen gas flows through line 33 and through catalyst charging conduit 21 to purge the reactor. Thereafter, the nitrogen may be used to charge catalyst into the reactor by flowing the nitrogen through an eductor under a catalyst hopper (not shown), to pick up the catalyst before it is introduced through line 33 into the catalyst charging conduit 21. After the catalyst is loaded into the reactor, it is purged with nitrogen. Additional catalyst is introduced with acetonitrile solvent during the process, as explained below.

Liquid dimethylamine (bp 7° C.), liquid VCl (bp −13° C.) and gaseous CO under sufficient pressure to maintain the mixed liquid and gaseous phase requirements of the reaction zone, are continuously fed through charging lines 22, 23 and 24 and flow control valves 25, 26 and 27 respectively, into charging manifold 28 which leads into the bottom of the reactor 10. Acetonitrile solvent is introduced into the reactor through a charging line 34 into the catalyst charging conduit 21. Acetonitrile is also introduced continuously to ensure that DMA.HCl salt is not deposited in the pores of the catalyst. During operation, the acetonitrile is used to carry make-up catalyst from the catalyst hopper through the eductor (not shown).

The reactants in the required molar ratios are fed to the reactor when it reaches operating temperature. The reactants contact the slowly stirred bed of catalyst and the reaction proceeds to form the Michael adduct and DMA.HCl. Conversion of DMA is adjusted to be ≦90%. The amount of DMA in the feed is the limiting reactant, and the reactor pressure is maintained by pressurizing with CO.

The catalyst, unconverted reactants, and reaction products leave the reactor as vapor and slurry near the top through discharge line 29 and are discharged into a continuous centrifuge 30 which separates the solid catalyst 20 and discharges it through line 31 for return to the reactor through catalyst conduit 21. Uncondensed VCl vapor and CO leaving the centrifuge 30 flow through line 35 into refrigerated condenser 36 where the VCl condenses and flows into separator drum 37. CO from drum 37 is vented through vent 39 and recycled (not shown). Liquid VCl from the drum 37 flows through line 38 and is combined with the VCl in line 51 for return to the reactor.

The liquid reaction products are discharged from the centrifuge through line 32 into flash drum 40. Acetonitrile, unreacted VCl, CO and DMA leave the top of the flash drum 40 through line 41 and are led into a condenser 42 in which acetonitrile is condensed. The liquid acetonitrile and the gaseous unreacted VCl and DMA flow through line 43 into flash drum 44. The liquid acetonitrile is returned to the reactor through line 45, pump 46 and line 47 which allows a choice of introducing the recycled acetonitrile either near the top of the reactor or its bottom, or distributed to both locations in a predetermined ratio through flow control valves (not shown). Gaseous VCl and DMA flow from the flash drum 44 to compressor 49 where they are compressed for return to the reactor.

After separation of the VCl, CO, acetonitrile and DMA in the flash drum 40, the remaining mixture of liquid Michael adduct and solid DMA.HCl are transferred into neutralizing tank 50 where the DMA.HCl is neutralized with an inorganic aqueous alkali, preferably alkali metal hydroxide such as 50% NaOH introduced through line 52. A slurry of DMA, salt such as sodium chloride and Michael adduct is withdrawn through line 53 and pumped with slurry pump 54 into a thermal cracker 60.

The thermal cracker 60 is provided with an electric heating jacket 61 which provides sufficient heat to crack the Michael adduct at a temperature in the range from 180° C. to 220° C. at which both DMA and NNDMA (bp 175° C.) are vaporized. Water vapor along with the DMA and NNDMA vapors flow through vapor line 62 into condenser 63 in which the NNDMA and water vapor is condensed at a temperature near 100° C. to minimize the re-formation of the adduct. The condensed NNDMA together with water and DMA vapors are led through line 64 into flash drum 65 where the condensed NNDMA and water is separated from DMA vapors. The DMA vapors are led through line 66 to the suction side of the compressor 49 for return to the reactor. The condensed, wet NNDMA product is removed through line 67 and preferably further cooled before being distilled and stored.

Hot sodium chloride which remains after the NNDMA and DMA are vaporized, is withdrawn from the bottom of the cracker through line 68 which is provided with a gate valve 69. At periodic intervals the valve is opened and the salt is discharged into lockhopper 70 from which it is removed through line 71, by a screw conveyor (not shown).

The following examples 1 and 2 illustrate the steps in the preparation of the phosphinated polystyrene.PdCl$_2$ amidation catalyst. Example 1 illustrates preparation of the phosphinated macroporous polystyrene, and example 2, the insertion of PdCl$_2$ to form the Pd(II) coordination complex. Examples 3–5 illustrate how the critical parameters which affect the rate of amidation of the VCl with DMA were discovered.

EXAMPLE 1

Preparation of Phosphinated, Macroporous Polystyrene

The macroporous polystyrene substrate used in the preparation of this catalyst has a particle size of 300–800 μm, is crosslinked with 3 mol % of divinyl benzene, and has an average pore size of 800 Å.

A 500 mL, 3-neck flask was fitted with an addition funnel, magnetic stir bar, gas bubbler, and wrapped with aluminum foil to exclude light. The flask was charged with 30.0 g of macroporous polystyrene, 300 mL of carbon tetrachloride, and 0.60 g (3.7 mmol) of anhydrous ferric chloride. The addition funnel was charged with 18.6 g (0.116 mol) of bromine dissolved in 75 mL of carbon tetrachloride. The polystyrene suspension was stirred for 1 hr, and the bromine-carbon tetrachloride solution was added over a 2 hr period. The mixture was stirred overnight, filtered through a sintered glass filter funnel, and washed with acetone until colorless. It was then washed with 100 mL of 2/1 ethanol/water, acetone, and dried 1 hr in a vacuum oven at room temperature, giving 38.35 g of brominated polystyrene.

A 500 mL, 3-neck flask was fitted with an argon inlet, septum, gas bubbler, magnetic stirring bar, and thermometer. The flask was charged with 38.35 g of brominated polystyrene (0.10 mol Br) and purged with argon. Dry toluene (100 mL) was injected followed by 156 mL (0.25 mol) of 1.6 N butyllithium. The mixture was stirred and heated at 60° C. for 3 hr. It was then cooled and the liquid phase removed through a sintered glass filter tube under argon. The contents were suspended in 75 mL of dry toluene, stirred, and the toluene removed in the same way. Dry THF (200 mL) was then added followed by 27.6 g (0.125 mol) of chlorodiphenylphosphine. After stirring at room temperature for 3 hr, the mixture was vacuum filtered and washed with 100 mL of each of the following: THF, ether, water, THF, methanol, and vacuum dried overnight. Elemental analysis showed 4.7% P (theor. 4.8%). Element mapping using SEM energy dispersive X-ray analysis showed a uniform distribution of phosphorous in the particle cross section and no residual chlorine.

EXAMPLE 2

Insertion of PdCl2: Preparation of Catalyst Where P/Pd=6 (Mol/Mol)

A 50 mL, 3-neck flask was fitted with an argon inlet, septum, and magnetic stirring bar. The flask was charged with 3.50 g of phosphinated polystyrene (3.51 mmol P), 0.224 g (0.585 mmol) $PdCl_2(PhCN)_2$, and purged with argon. Methylene chloride (30 mL) was injected and the mixture stirred at room temperature for 45 min, as the solution became colorless. The mixture was vacuum filtered, washed with methylene chloride, and returned to the flask and resuspended with an additional 30 mL of methylene chloride. It was again filtered, washed with methylene chloride, and vacuum dried overnight at room temperature, giving a light orange-colored solid.

EXAMPLE 3

Amidation of VCl with $HN(CH_3)_2$ and Catalyst Where P/Pd=6

The 500 mL stainless steel pressure reactor containing a glass liner was charged with 2.22 g of the catalyst (0.36 mmol Pd) and evacuated. VCl (19.1 g) was then charge in the usual way followed by venting of 800 mL of VCl gas to purge the line. This was followed by an injection of 33 mL of dry acetonitrile. Acetonitrile is added to maintain DMA hydrochloride in solution. DMA (5.30 g, 0.118 mol) and CO (partial pressure of 250 psi) were then charged. Amidation was performed at 90° C. where the initial pressure was 400 psi.

The conversion of DMA was followed by gas chromatography using a 10'×⅛" Carbopak column with a helium flow rate of 52 mL/min operating at 35° C. (4 min) followed by a program to 90° C. at 30° C./min. Gas samples are diluted with nitrogen to prevent condensation of acetonitrile. H-NMR quantitation for the reaction product, 3-dimethylamino-N,N-dimethylpropanamide, is performed on the D20 extract of the dry reaction product using the N,N-dimethylamido resonance at δ3.12 and added tert-butanol as the internal standard. Titration for Cl- is performed in the usual way.

Gas chromatographic analyses showed that very little amidation occurred over 146 minutes.

EXAMPLE 4

Amidation of VCl With $HN(CH_3)_2$ and Catalyst Where P/Pd=4

The procedure described in example 3 above, for the preparation of the P/Pd=6 catalyst was repeated but with 0.337 g (0.878 mmol) of $PdCl_2(PhCN)_2$ instead of 0.224 g. VCl amidation was then performed in the same way as in example 3 using 1.5 g of this catalyst (0.36 mmol Pd).

Again, gas chromatographic analysis showed that little reaction occurred over a total of 345 min.

EXAMPLE 5

Amidation of VCl With $HN(CH_3)_2$ and Catalyst Where P/Pd=2

The procedure described in example 4 above for the preparation of the P/Pd=6 catalyst was repeated but with 0.675 g (1.76 mmol) of $PdCl_2(PhCN)_2$ instead of 0.224 g. Elemental analysis showed 4.4% Pd (theor. 4.9%). VCl amidation was then performed in the same way as example 4 using 1.14 g of catalyst (0.473 mmol Pd). Unlike the earlier examples, this catalyst was found to be active. The rate based on DMA consumed was $1.9 \times 10^{-4}$ $mol$min$^{-1}$ (turnover rate, 24 hr$^{-1}$). At approximately 80% conversion of DMA, the reactor was cooled in ice, recharged with VCl, DMA, and carbon monoxide in the amounts consumed, and the reactor reheated to 90° C. to resume the reaction. This step was performed a total of five times with a total reaction time of 43 hrs. During the recharging steps, the rate of DMA consumption ranged from 2.9 to $4.2 \times 10^{-4}$ mol DMA/min. The experiment was stopped because the rate began to decline after this period, likely due to the accummulation of large amounts of reaction products, including DMA hydrochloride. The reaction mixture was a viscous mass. Titration for Cl-showed that 0.138 mole of VCl had reacted during this period (theor. 11.1 g of DMA.HCl). Quantitative H-NMR showed that 0.126 mole of 3-dimethylamino-N,N-propanamide was produced (91% yield). Elemental analysis of the recovered catalyst showed 3.92% Pd, 89% retention.

Having thus provided a general discussion, described the overall process in detail and illustrated the invention with specific examples of the best mode of carrying out the process, it will be evident that the invention has provided an effective solution to a difficult problem. It is therefore to be understood that no undue restrictions are to be imposed by reason of the specific embodiments illustrated and discussed, except as provided by the following claims.

I claim:

1. In the amidation of vinyl chloride with dimethylamine to produce N,N-dimethylacrylamide, a two step continuous process comprising, in a first step, reacting a stoichiometric excess of vinyl chloride and carbon monoxide with dimethylamine in the presence of a catalytically effective amount of a heterogeneous catalyst consisting essentially of a porous support having covalently bonded triorganophosphines forming coordination complexes with Pd(0) or a Pd(II) complex capable of being reduced to Pd(0) under amidation conditions, said Pd(0) complex having the stoichiometry:

$Pd(PR_3)_n$ wherein

R represents $C_1$–$C_4$ lower alkyl, phenyl, $C_1$–$C_4$ alkylphenyl, and cycloalkyl having 4 to 6 ring carbon atoms;

n is an integer in the range from 2 to 6; and, when n>4 excess ligand is present;

under elevated temperature and pressure reaction conditions, to form a major amount, on a molar basis, of the Michael adduct of said dimethylamine with said N,N-dimethylacrylamide, said conditions being a temperature in the range from above 80° C. to a temperature below which said Michael adduct dissociates, and under a pressure in the range from about 200 psig but below 600 psig; and, in a second step, converting said Michael adduct to said N,N-dimethylacrylamide.

2. The process of claim 1 wherein said support is selected from a macroporous cross-linked swellable synthetic resin having a pore size in the range from about 500 Å to about 2000 Å, and a microporous siliceous particulate material having a pore size in the range from about 50 Å to about 100 Å.

3. The process of claim 1 comprising, in said first step, adding a solvent for DMA.HCl in an amount sufficient to prevent pores of said support from being blocked.

4. The process of claim 3 wherein said ratio of P/Pd is in the range from 2 to 4, and comprising, in said second step, heating said Michael adduct to its dissociation temperature in the range from about 170° C. to 220° C.

5. The process of claim 4 comprising, in said second step, returning said dimethylamine obtained from dissociation of said Michael adduct to said first step.

6. The process of claim 3 wherein said support is crosslinked polystyrene having a pore size in the range from about 700 Å to about 900 Å.

7. The process of claim 3 wherein said solvent is acetonitrile.

8. A continuous process for the catalytic production of N,N-dimethylacrylamide, comprising, reacting a stoichiometric excess of vinyl chloride and carbon monoxide with dimethylamine in the presence of a catalytically effective amount of a heterogeneous catalyst consisting essentially of a porous support having covalently bonded triorganophosphines forming coordination complexes with Pd(0) or a Pd(II) complex capable of being reduced to Pd(0) under amidation conditions, the Pd(0) complex having the stoichiometry:

$Pd(PR_3)_n$ wherein

R represents $C_1-C_4$ lower alkyl, phenyl, $C_1-C_4$ alkylphenyl, and cycloalkyl having 4 to 6 ring carbon atoms;

n is an integer in the range from 2 to 6; and, when n>4, excess ligand is present;

in a reaction zone at a temperature in the range from above 80° C. to a temperature below which the Michael adduct dissociates, and under a pressure in the range from about 200 psig but below 600 psig, to form a major amount, on a molar basis, of the Michael adduct of the dimethylamine with the N,N-dimethylacrylamide in the presence of a solvent for dimethylamine hydrochloride (DMA.HCl);

recovering the Michael adduct and DMA.HCl together with solvent, from the reaction products of reaction, and venting excess carbon monoxide;

separating the solvent from the Michael adduct and DMA.HCl and returning the solvent to the reaction zone;

adding a sufficient amount of an inorganic aqueous alkali to neutralize the DMA.HCl and form an inorganic salt;

recovering the inorganic salt;

heating the Michael adduct to above its dissociation temperature to form N,N-dimethylacrylamide and dimethylamine;

cooling the N,N-dimethylacrylamide and dimethylamine at a temperature above that which will provide favorable conditions for the Michael adduct to be re-formed;

recovering the N,N-dimethylacrylamide; and, returning said dimethylamine from the Michael adduct to the reaction zone.

9. The process of claim 8 including recovering dimethylamine contaminated with vinyl chloride from the reaction products and returning them to the reactor.

10. The process of claim 9 wherein said support is selected from a macroporous cross-linked swellable synthetic resin having a pore size in the range from about 500 Å to about 2000 Å, and a microporous siliceous particulate material having a pore size in the range from about 50 Å to about 100 Å.

11. The process of claim 10 comprising adding enough of said solvent to prevent pores of said support from being blocked.

12. The process of claim 11 wherein said ratio of P/Pd is in the range from 2 to 4, and comprising heating said Michael adduct to its dissociation temperature in the range from about 170° C. to 220° C.

13. The process of claim 12 wherein said support is crosslinked polystyrene having a pore size in the range from about 700 Å to about 900 Å.

14. The process of claim 12 wherein said solvent is acetonitrile.

15. The process of claim 13 wherein said solvent is acetonitrile.

16. The process of claim 12, comprising returning said carbon monoxide to said reaction zone.

* * * * *